United States Patent
Lieberman et al.

[11] Patent Number: 6,115,061
[45] Date of Patent: *Sep. 5, 2000

[54] IN SITU MICROSCOPE IMAGING SYSTEM FOR EXAMINING SUBSURFACE ENVIRONMENTS

[75] Inventors: Stephen H. Lieberman, La Mesa; David S. Knowles; Leonard J. Martini, both of San Diego, all of Calif.

[73] Assignee: The United States of America as represented by the Secretary of the Navy, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/772,611

[22] Filed: Dec. 23, 1996

Related U.S. Application Data

[63] Continuation-in-part of application No. 08/630,653, Apr. 10, 1996, abandoned.

[51] Int. Cl.[7] ........................................... H04N 7/18

[52] U.S. Cl. .................................. 348/85; 175/49

[58] Field of Search .................... 436/28; 348/85, 348/148, 135; 358/100; 122/379; 134/1; 359/834, 386; 73/151; 175/4.6, 49; 166/242.1; 356/32; 118/315

[56] References Cited

U.S. PATENT DOCUMENTS

| | | | |
|---|---|---|---|
| 3,992,095 | 11/1976 | Jacoby et al. | 356/32 |
| 4,130,085 | 12/1978 | Hewitt | 118/315 |
| 4,391,337 | 7/1983 | Ford et al. | 175/4.6 |
| 4,532,544 | 7/1985 | Federau | 358/87 |
| 4,666,672 | 5/1987 | Miller et al. . | |
| 4,696,903 | 9/1987 | Owen . | |
| 4,779,201 | 10/1988 | Iizuka et al. | 702/10 |
| 4,805,450 | 2/1989 | Bennett et al. . | |
| 4,855,820 | 8/1989 | Barbour | 358/100 |
| 4,899,277 | 2/1990 | Iizuka et al. | 702/6 |
| 4,899,697 | 2/1990 | Franklin et al. | 122/379 |
| 4,929,562 | 5/1990 | Anderson et al. . | |
| 4,954,318 | 9/1990 | Yafuso et al. . | |
| 4,980,278 | 12/1990 | Yamada et al. . | |

(List continued on next page.)

OTHER PUBLICATIONS

"Pressurized Membrane Indicator System For Fluorogenic–Based Fiber–Optic Chemical Sensors", S. M. Inman et al.

"Rapid, Subsurface, In Situ Field Screening of Petroleum Hydrocarbon Contamination Using Laser Induced Fluorescence Over Optical Fibers", Symposium Proceedings, 12–14 Feb. 12–14, 1991, Las Vegas, NV, pp. 57–63.

"Development of a pulsed–laser, fiber–optic–based fluorimeter: determination of fluorescence decay times of polycyclic aromatic hydrocarbons in sea water", Scott M. Inman et al.

*Primary Examiner*—Chris S. Kelley
*Assistant Examiner*—Tung Vo
*Attorney, Agent, or Firm*—Harvey Fendelman; Peter A. Lipovsky; Michael A. Kagan

[57] ABSTRACT

A microscope imaging system comprises a tube including a bore and a sidewall having an aperture; an optically transparent window positioned in the aperture; a light source for generating first light signals which are directed at diffuse angles through the window; an imaging system mounted in the bore for detecting second light signals which enter the bore through the window; and a first lens system for focusing the second light signals onto the imaging system. The system may also include a focusing system for changing the distance between the imaging system and the first lens system, and a fluid delivery system for ejecting a chemical indicator reagent from the probe as it is being deployed through the ground. The reagent is dispersed from the tube in the vicinity of the optical window so that it comes into direct contact with the soil outside the tube near the window. The reagent reacts with a chemical or biological constituent of interest that may be present in the soil to produce a detectable optical response when exposed to a suitable light source.

39 Claims, 23 Drawing Sheets

U.S. PATENT DOCUMENTS

| | | | |
|---|---|---|---|
| 5,005,005 | 4/1991 | Brossia et al. | |
| 5,123,492 | 6/1992 | Lizanec, Jr. | |
| 5,128,882 | 7/1992 | Cooper et al. | |
| 5,154,197 | 10/1992 | Auld et al. | 134/1 |
| 5,246,862 | 9/1993 | Grey et al. | 436/28 |
| 5,316,950 | 5/1994 | Apitz et al. | |
| 5,353,870 | 10/1994 | Harris | 166/68 |
| 5,394,268 | 2/1995 | Lamni et al. | 359/386 |
| 5,439,800 | 8/1995 | Thompson | 436/28 |
| 5,520,046 | 5/1996 | Sornein et al. | 73/151 |
| 5,543,972 | 8/1996 | Kamewada | 359/834 |
| 5,652,617 | 7/1997 | Barbour | 348/85 |
| 5,767,400 | 6/1998 | Nakano et al. | 73/152.46 |

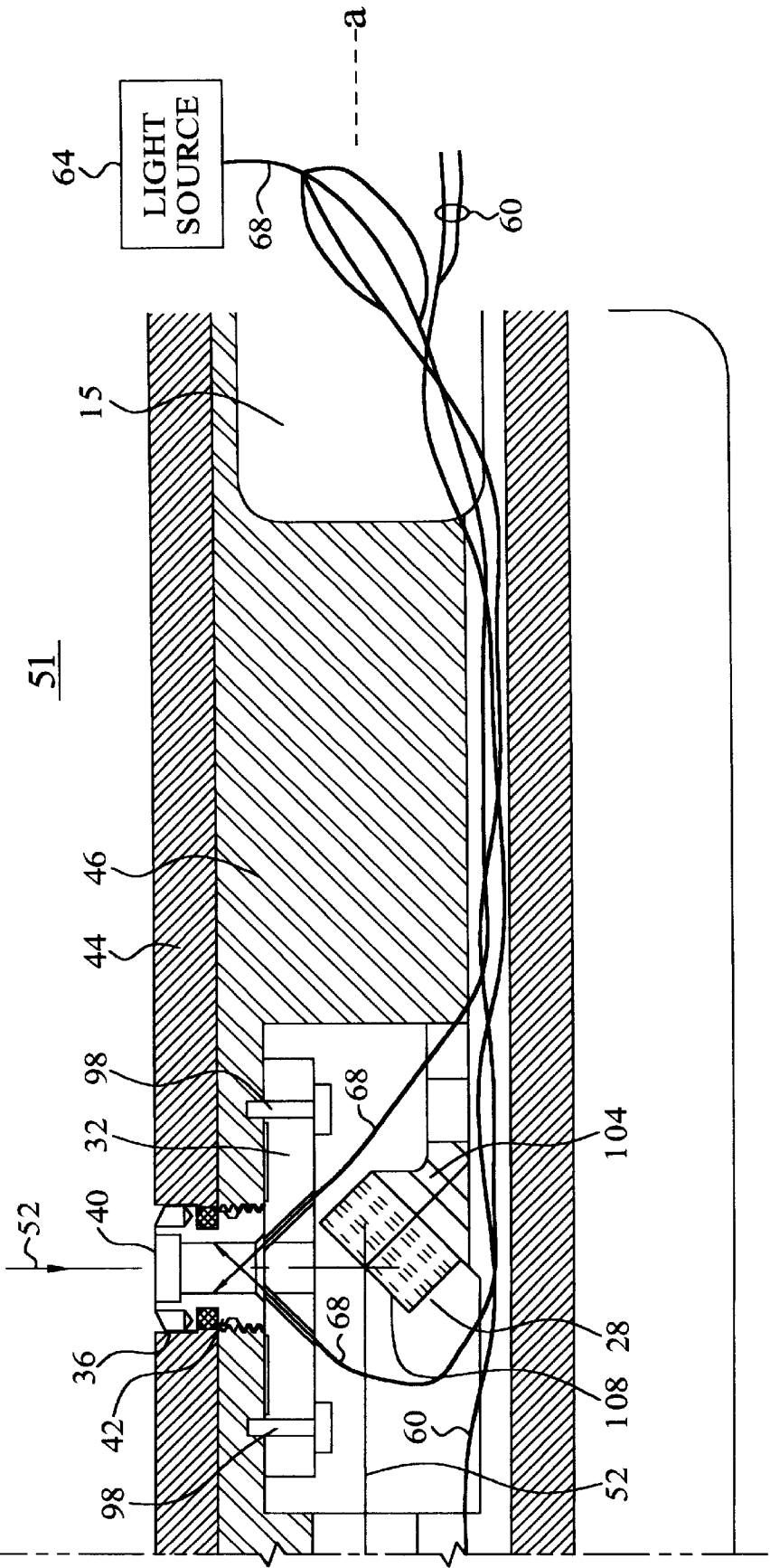

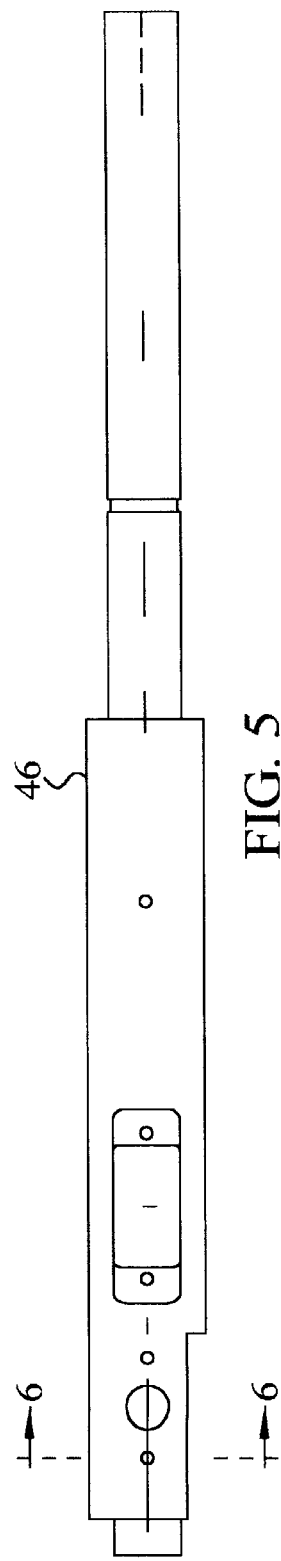
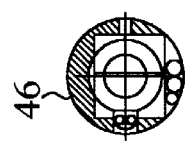
FIG. 5
FIG. 6

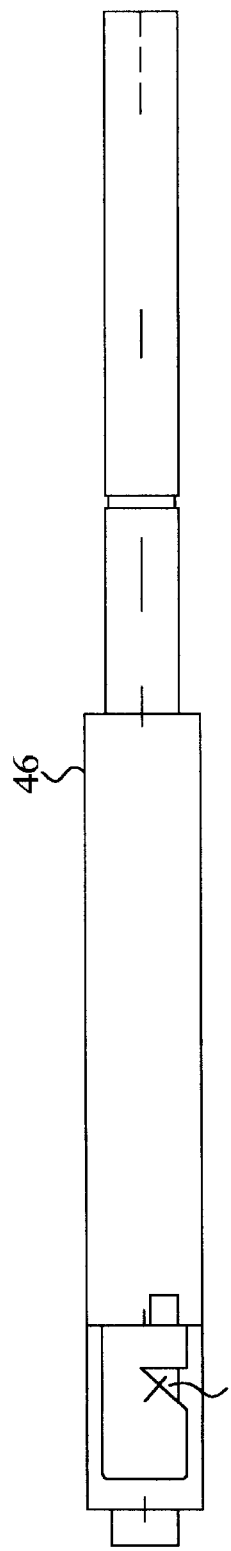
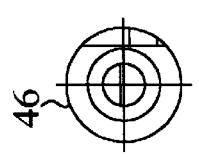
FIG. 7
FIG. 8

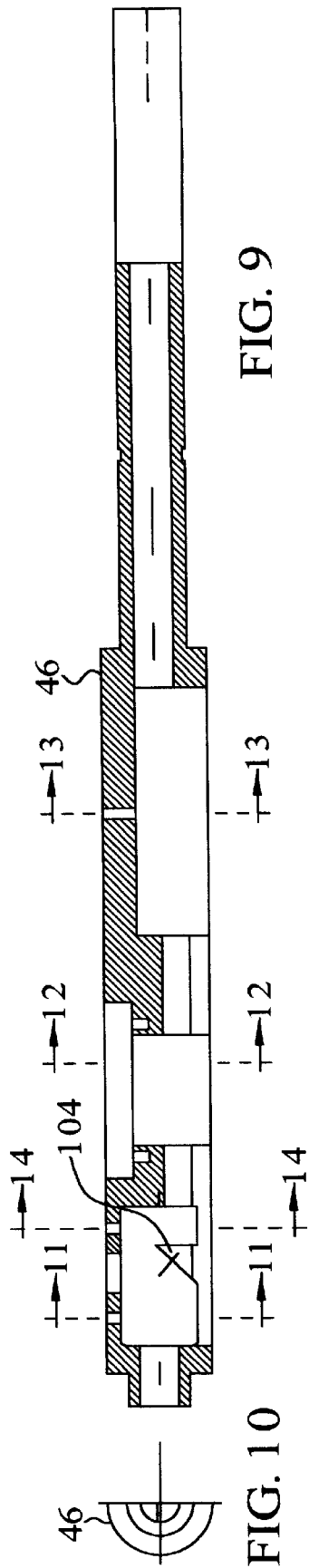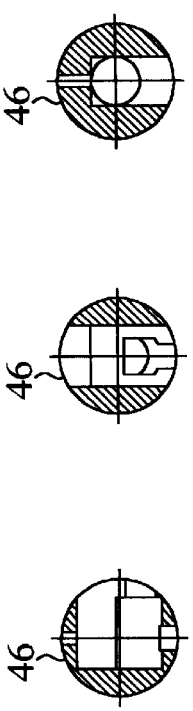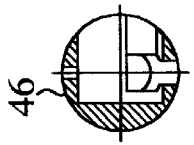
FIG. 9
FIG. 10
FIG. 11
FIG. 12
FIG. 13
FIG. 14

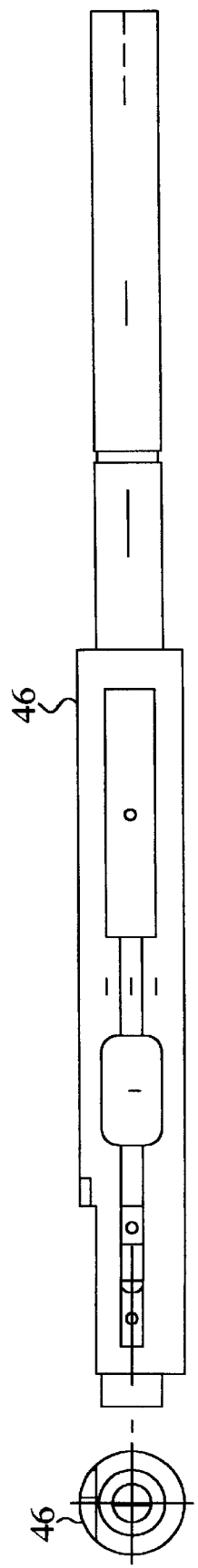

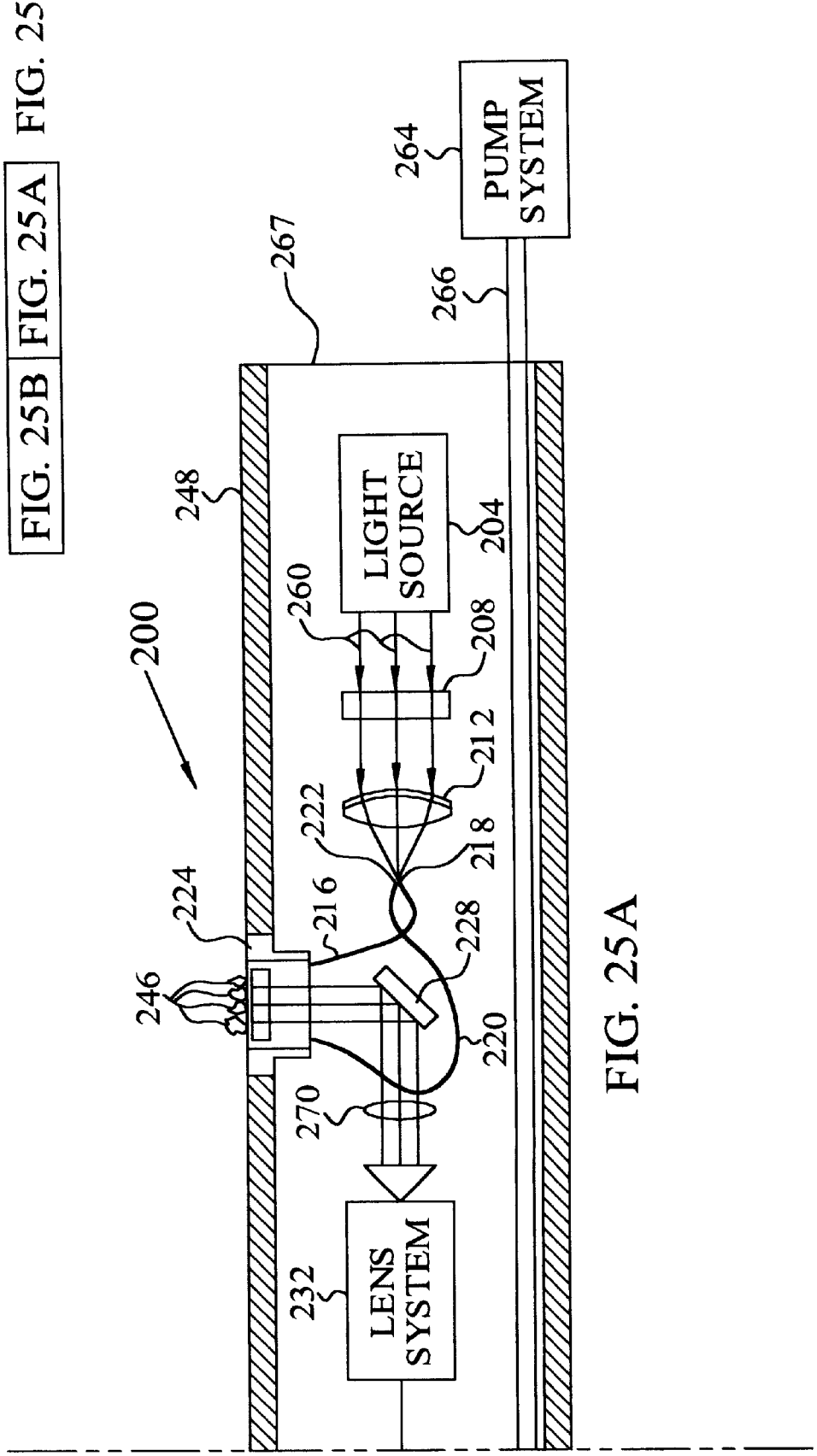

IN SITU MICROSCOPE IMAGING SYSTEM FOR EXAMINING SUBSURFACE ENVIRONMENTS

This application is a continuation-in-part of application Ser. No. 08/630,653 filed Apr. 10, 1996, now abandoned.

FIELD OF THE INVENTION

The present invention relates to a system for examining subsurface environments, and more particularly, to a microscope mounted in a soil penetrating probe for detecting visual images of subsurface geological environments.

BACKGROUND OF THE INVENTION

Increasing concern with soil and groundwater contamination and governmental mandated requirements to clean up hazardous waste sites have created a need for cost effective systems and methods for determining the characterization of subsurface environments. In response to such needs, soil penetrating probes have been developed. Soil penetrating probes generally comprise a tube having a tapered tip which is forced down into the ground. Instrumentation in the tube detects various properties of the surrounding geological environment.

U.S. Pat. No. 5,128,882, "DEVICE FOR MEASURING REFLECTANCE AND FLUORESCENCE OF IN-SITU SOIL," describes a soil penetrating probe having an optical fiber, a light source within the interior of the probe, and a transparent window which provides a light port into and out of the probe. Light passes through the transparent window to irradiate the surrounding soil immediately outside of the window as the probe passes through the soil. The irradiated soil reflects light back through the window whereupon the reflected light is collected by a fiber optic link connected to instrumentation on the surface. The collected light then is subjected to spectroanalysis for determining the chemical composition of the soil, particularly with regard to soil contamination. This system only detects the spectral characteristics of the surrounding environment; It cannot provide optical images. Therefore, information such as the porosity and grain size of surrounding soils are not discernible from the type of information provided through spectral analysis. However, porosity and grain size are important characteristics because they are important variables that control the transport of contaminants in soil.

Another soil penetrating probe system is described in U.S. Pat. No. 5,123,492, "METHOD AND APPARATUS FOR INSPECTING SUBSURFACE ENVIRONMENTS." This system includes a soil penetrating probe having a clear tube in which is suspended a video camera linked to the surface. A significant limitation of this system is that because the camera freely swings within the transparent tube, the focus of the camera with respect to the surrounding geological features is constantly changing and cannot be controlled. Furthermore, the system does not provide any means for illuminating the surrounding subsurface environment other than from ambient light which may happen to filter from the surface down through the tube.

Therefore, a continuing need exists for a system which can provide clear, sharply focused optical images of subsurface geological environments.

SUMMARY OF THE INVENTION

A microscope imaging system comprises a tube including a bore and a sidewall having an aperture; an optically transparent window positioned in the aperture; a light source for generating first light signals which are directed at diffuse angles through the window; an imaging system mounted in the bore for detecting second light signals which enter the bore through the window; and a first lens system for focusing the second light signals onto the imaging system. The system may also include a focusing system for changing the distance between the imaging system and the first lens system.

The invention provides a system that can be used to detect soil properties such as type of soil, grain size, color, porosity, presence or absence of fluid between soil particles, and volumetric density. Moreover, such properties can be detected in real time when the imaging system is implemented as a video camera. The invention advantageously images soil in contact with the probe, thereby establishing the focal distance of the image which is to be detected. Another advantage is that the invention may be used to investigate soil properties at spatial scales as small as individual soil particles. Moreover, the fact that the magnification factor and focal distance of the image are defined and fixed by the relationship of the camera to the window allows for quantification of soil particle size. An important feature of the invention is that it indirectly illuminates the soil through the window housing so as to provide sufficient light to illuminate the soil and to prevent saturation of the image detector from excessive light reflected back through the window.

In another embodiment, the invention further includes a fluid delivery system for ejecting a chemical indicator reagent from the probe as it is being deployed through the ground. The reagent is dispersed from the probe in the vicinity of the optical window so that it comes into direct contact with the soil outside the probe in the vicinity immediately adjacent to the window. The reagent reacts with the chemical constituent of interest (analyte) in the soil to produce a detectable optical response when exposed to a suitable light source. The operation of the invention is based on the fact that in the absence of the indicator reagent, no optical response is observable for certain types of chemical and/or biological species of interest. However, when a species of interest is present and reacts with the indicator reagent, a new compound is formed that may be optically detected so that the presence of the species of interest then may be ascertained. The probe may be pushed into the ground to a depth on the order of up to about 150 feet using a hydraulic ram while the indicator reagent is pumped out of the probe at a predetermined flow rate. In order to account for the possible variations in the amount of indicator reagent dispensed into the surrounding soil structure, a second chemical tracer can be added to the indicator reagent. The chemical tracer is non-reactive with the analyte and is spectroscopically distinguishable from the product of the species of interest and indicator reagent. The chemical tracer normalizes the concentration of indicator reagent added to the soil sample to correct for changes in optical response due to differences in the concentration of indicator present in the soil.

The indicator reagent delivery system extends the capabilities of the in situ sensor to detect chemical contaminants in subsurface soil environments that cannot presently be measured by direct optical methods. By continually dispensing the indicator reagent into the sample, or surrounding soil structure, problems associated with mechanical, chemical, and photochemical degradation of the indicator are simplified or eliminated.

These and other advantages of the invention will become more apparent upon review of the accompanying text taken in conjunction with the drawings.

BRIEF DESCRIPTION OF THE DRAWINGS

FIGS. 3A, 3B, 3C and 3D (collectively referenced as FIG. 3) are a schematic view of an example of in-situ microscope for examining subsurface environments embodying various features of the present invention.

FIG. 5 is a full length view of the terminator insert.

FIG. 6 is a cross-sectional view of the terminator insert taken along line 6—6 of FIG. 5.

FIG. 7 shows another full length view of the terminator insert.

FIG. 8 is an end view of the terminator insert of FIG. 7.

FIG. 9 is a cross-sectional view taken along the length of the terminator insert.

FIG. 10 is another end view of the terminator insert of FIG. 9.

FIG. 11 is a cross-sectional view of the terminator insert taken along line 11—11 of FIG. 9.

FIG. 12 is a cross-sectional view of the terminator insert taken along line 12—12 of FIG. 9.

FIG. 13 is a cross-sectional view of the terminator insert taken along line 13—13 of FIG. 9.

FIG. 14 is a cross-sectional view of the terminator insert taken along line 14–14 of FIG. 9.

FIG. 15 is another full length view of the terminator insert.

FIG. 16 is an end view of the terminator insert shown in FIG. 15.

FIGS. 25A and 25B (collectively referenced as FIG. 25 ) show an in situ optical detection system further including an indicator reagent delivery system.

Throughout the several figures like elements are referenced using like reference numbers.

DESCRIPTION OF THE PREFERRED EMBODIMENTS

The invention provides a microscope imaging system for remotely detecting optical images of subsurface geological structures such as soil particles. Imaging is accomplished by illuminating the soil in contact with the outside of an optically transparent window installed in a soil penetrating probe and then imaging the soil using a miniaturized imaging system such as a camera supported in the probe. A signal representing the images is provided by the camera and conveyed to the surface where it may be displayed on a TV monitor, recorded on a VCR and/or recorded digitally using a video frame grabber coupled to a microcomputer system.

Important features of the invention include: (1) an illumination system that provides light to illuminate geological structures of interest so that the camera may be usefully operated in what would otherwise be a dark environment; (2) a lens system optically coupled to an optically transparent window installed in the soil penetrating probe so that the magnification factor and focal distance of a detected image are both known and fixed for geological features in contact with the window. The fact that the magnification factor of the soil particles imaged by the camera is known facilitates measurement of the grain size of soil particles from analysis of the image. The use of different lenses in the magnification system makes changes readily possible in the magnification factor of the imaging system.

Figure 1:
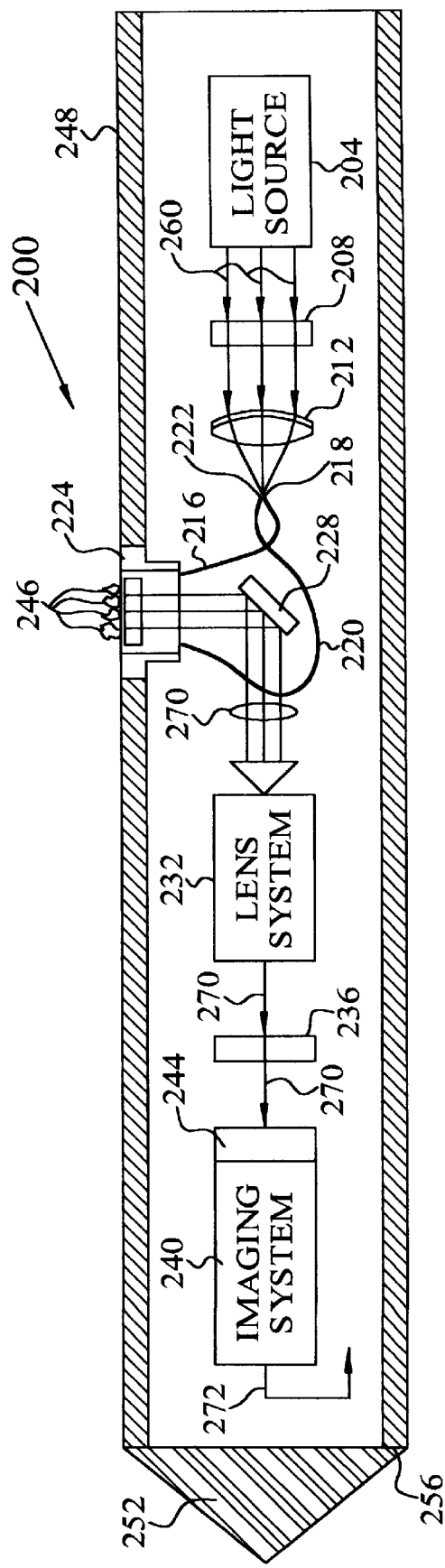
FIG. 1 is a schematic illustration of an in-situ microscope embodying various features of the present invention.
Figure 2:
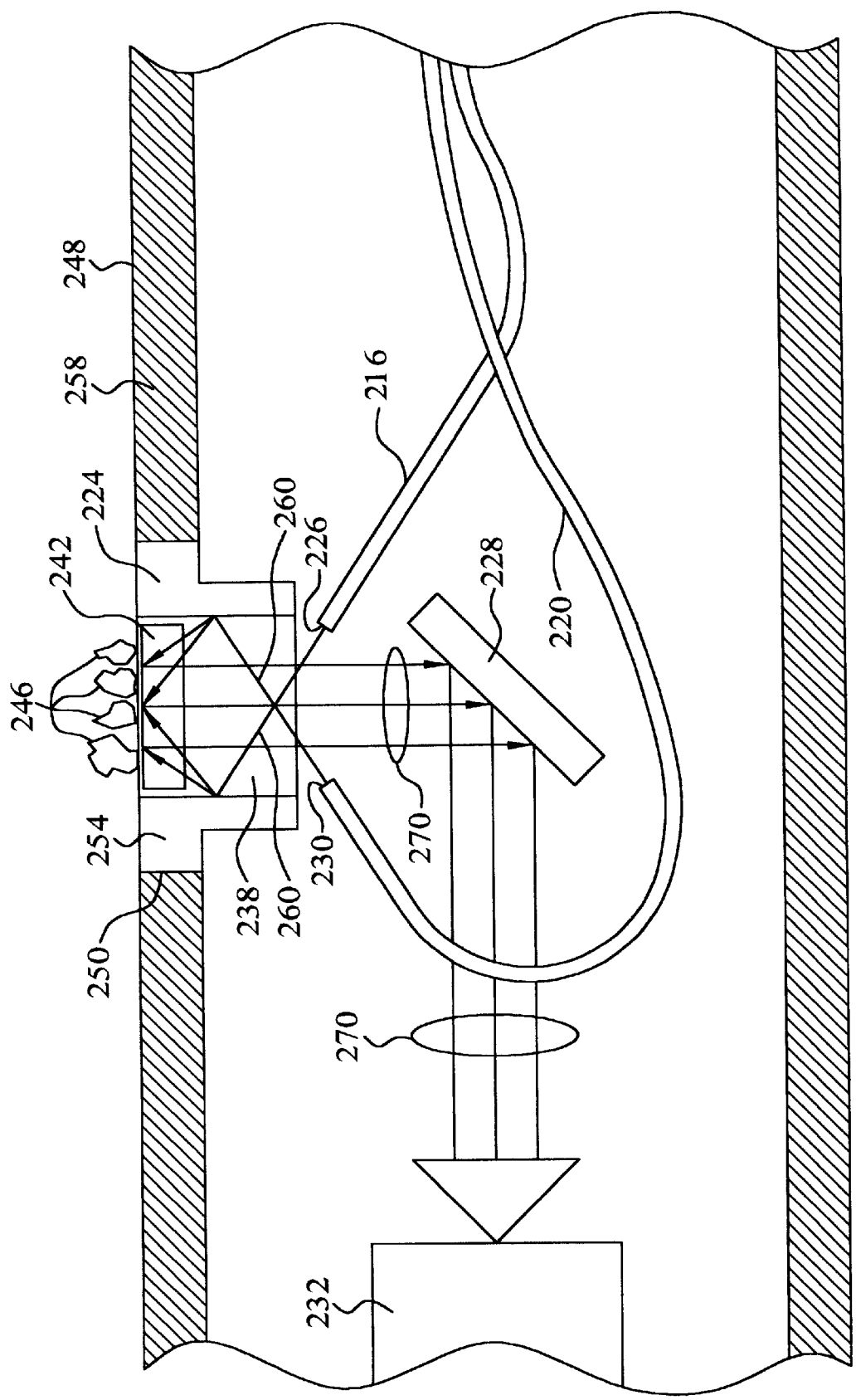
FIG. 2 is an enlarged view of the window housing of the microscope represented in FIG. 1.
Figure 31:
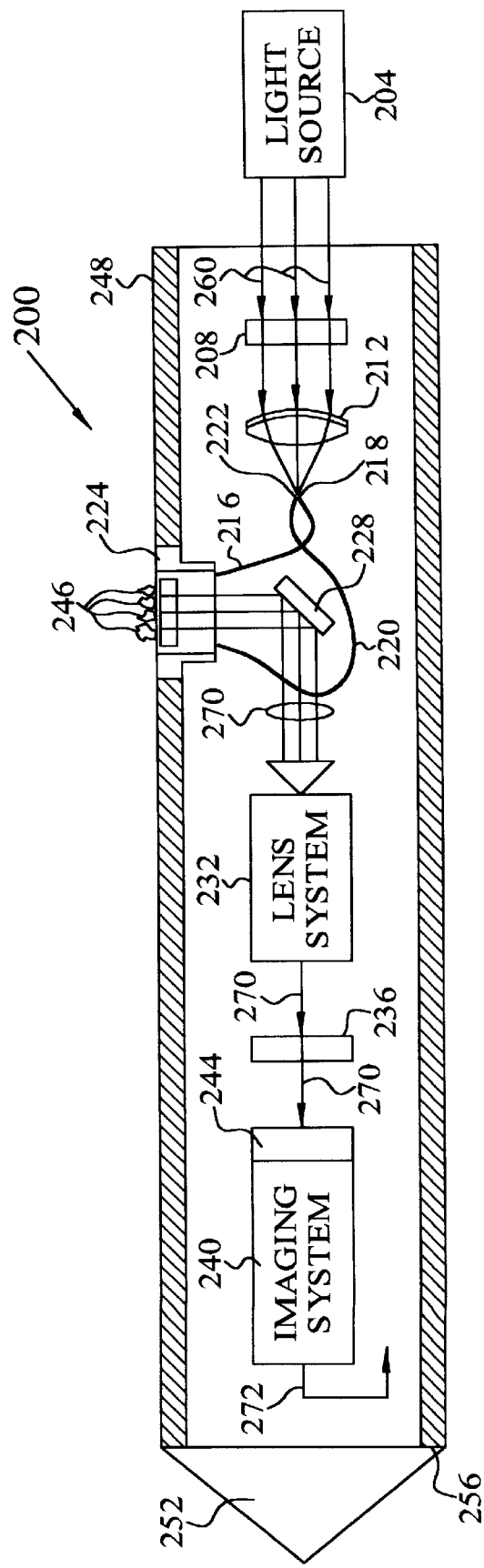
FIG. 31 is a schematic illustration of an in-situ microscope where the light source is located remotely from the tube.

In FIGS. 1 and 2 there is shown an in-situ microscope imaging system 200 which includes a light source 204, an optional optical filter 208, a focusing lens 212, optical fibers 216 and 220, window housing 224, optical reflecting element 228, lens system 232, optional optical filter 236, and imaging system 240, such as a still camera or video camera, having an image detecting area 244, all mounted in a tube 248 having a throughbore 262. A conically shaped tip 252 is mounted to the penetration end 256 of the tube 248. The optical reflecting element 228 may be implemented as a prism or mirror. The window housing 224 includes an insert fitting 254 and a transparent window 242. The insert fitting is fitted through an aperture 250 of sidewall 258 of tube 248. The surface 234 of bore 238 preferably has a surface finish which when illuminated, causes light to be diffused in different directions. The light source 204 may be implemented, for example, as a laser, flash lamp, arc-lamp, or any other source of optical energy that generates light at wavelengths suitable for a particular application. When implemented as a laser, the light source 204 may be a nitrogen, xenon-chloride, Nd-YAG, or other suitable laser. Lens system 232 may have a fixed focal length or may have a motor driven "zoom" type lens to provide the lens system with an adjustable focal length. In FIG. 1, the light source 204 is shown positioned in the tube 248. However, there may be applications where it is desirable for the light source 204 is located remote from the tube 248, as shown in FIG. 31.

Referring to FIG. 1, light source 204 generates light signals 260 which are directed to focusing lens 212. In some applications, optical filter 208 optionally may be interposed between the lens 212 and light source 204 to filter out undesirable spectral components or to select specific components, having particular wavelengths, of the light signals 260. Lens 212 focuses light signals 260 onto the bare polished, and preferably bundled ends 218 and 222 of optical fibers 216 and 220, respectively. Light signals 260 propagate through optical fibers 216 and 220. Then, as shown in FIG. 2, the light signals 260 are emitted from the ends 226 and 230 of optical fibers 216 and 220, respectively. Fibers 216 and 220 may be implemented as Ensign-Bickford HCG fiber having a 365 micro meter diameter, although it is to be understood that other fibers having other diameters may also be used. The light signals 260 illuminate the sidewall, 234 of bore 238 and are directed at diffuse angles through transparent window 242 to illuminate soil particles 246 outside the window 242. In the preferred embodiment, transparent window 242 may be made of sapphire because it is optically transparent over a broad spectral range and is very hard. The hardness of the window 224 is important in order for the window to withstand the rigors of abrasion as the tube 248 penetrates the soil.

Still referring to FIG. 2, light signals 260 illuminate the soil particles 246. Light signals 270 radiating from illuminated soil particles 246 are reflected by optical reflecting element 228 and directed to lens system 232. As shown in FIG. 1, lens system 232 focuses the light signals 270 onto image gathering area 244 of imaging system 240. Optionally, optical filter 236 may be interposed between the focusing system 232 and the imaging system 240 to selectively filter undesirable spectral components or to select specific components, having particular wavelengths, of the light signals 270. The image system transforms signals 270 into an output signal 272 which represents an image of the soil particles 246. The output signal may be provided to signal processing equipment, not shown, at the earth's surface.

An example of one particular implementation of the present invention is described with reference to FIG. 3. An in-situ microscope optical imaging system 10 for examining subsurface geological environments includes a soil penetrating probe 12 comprised of a tube 14 and a hardened, conical tip 16 mounted to the penetration end 18 of the tube 14. Inside the tube are mounted a camera 20, such as a video camera which may include a charge coupled device (CCD), a lens system 24, an optically reflective element, such as a mirror 28 or a prism, and an illumination system 32. Examples of video cameras suitable for use in conjunction with the present invention are Sony Corporation Model XC777 ⅓" CCD and Model XC999 ½" CCD. Each of these Sony cameras has a 768×494 pixel array. Referring also to FIG. 4, a window housing 36, having a transparent window 40 and bore 49, is fitted through an aperture 42 in the wall 44 of the tube 14 to provide a viewing port between the interior bore 15 of the tube 14 and exterior 51 of the tube 14. The window housing is mounted to the tube 14 as explained further herein. Window housing 36 has an annular groove 76 in which is fitted O-ring 80 to provide a dirt and moisture seal between the window housing 36 and the sidewall 44 of tube 14.

In FIG. 4, light signals 48 are shown emitted from within the tube 14 at diffuse angles through transparent window 40 with respect to the longitudinal axis a—a of the penetrometer 12. Light signals 48 become scattered (i.e., diffused) after illuminating the surface 47 of bore 49 in window housing 36. The diffused light signals 48 are directed through the window 40 to illuminate the surrounding geological structures, not shown. Light signals 52 radiated from surrounding geological structures (not shown) outside transparent window 40 return through the window 40, reflect off mirror 28, and are directed to lens system 24, such as a Sony Corporation 45 mm macro lens. The surface 47 preferably has a finish which causes light signals to become diffused, and may for example, have a surface finish of 250 micro inches r.m.s. so that the surrounding geological structures are illuminated with diffused light to prevent saturation of the imaging system 20. In the preferred embodiment, light signals 48 are provided by a light source 64.

Lens system 24 focuses light signals 52 which radiate into the tube 14 through window 40 and are directed onto the image gathering area 56 of the camera 20. Image signals generated by the camera 20 represent the detected image of geological structures outside window 40 and are provided to the surface, not shown, by signal line 60. Optionally, the preferred embodiment may include a focusing system 72 for changing the relative position of the image gathering area 56 of camera 20 with respect to the lens system 24 in order to precisely focus light signals 52 onto the image-gathering area 56 of camera 20.

As shown in FIG. 4, an illumination plate 88 is mounted to a terminator insert 46 preferably by bolts 98. The distal ends 69 of optical fibers 68 are mounted within bores 70 of illumination plate 88 at an angle whereupon light signals 48 illuminate the sidewall 47 of bore 49 in window housing 36 with diffused light. The axes of the bores 70 are at an angle theta, as for example 45 degrees, with respect to the longitudinal axis a—a of the tube 14. The terminator insert 46, shown by way of example in FIGS. 5–16, slides within bore 15 of tube 14 and supports the window housing 36 in the bore 42 of the tube 14. FIG. 4 shows that the illumination plate 88 includes a center bore 96 having a longitudinal axis b—b which preferably is coaxially aligned with bore 49 of the window housing 36 to provide a light port into and out of the bore 15 of tube 14. The opposite ends of illumination plate 88 include apertures 95 through which threaded connecting elements 98 are fitted to attach the illumination plate 88 to the terminator insert 46.

Figure 3B:
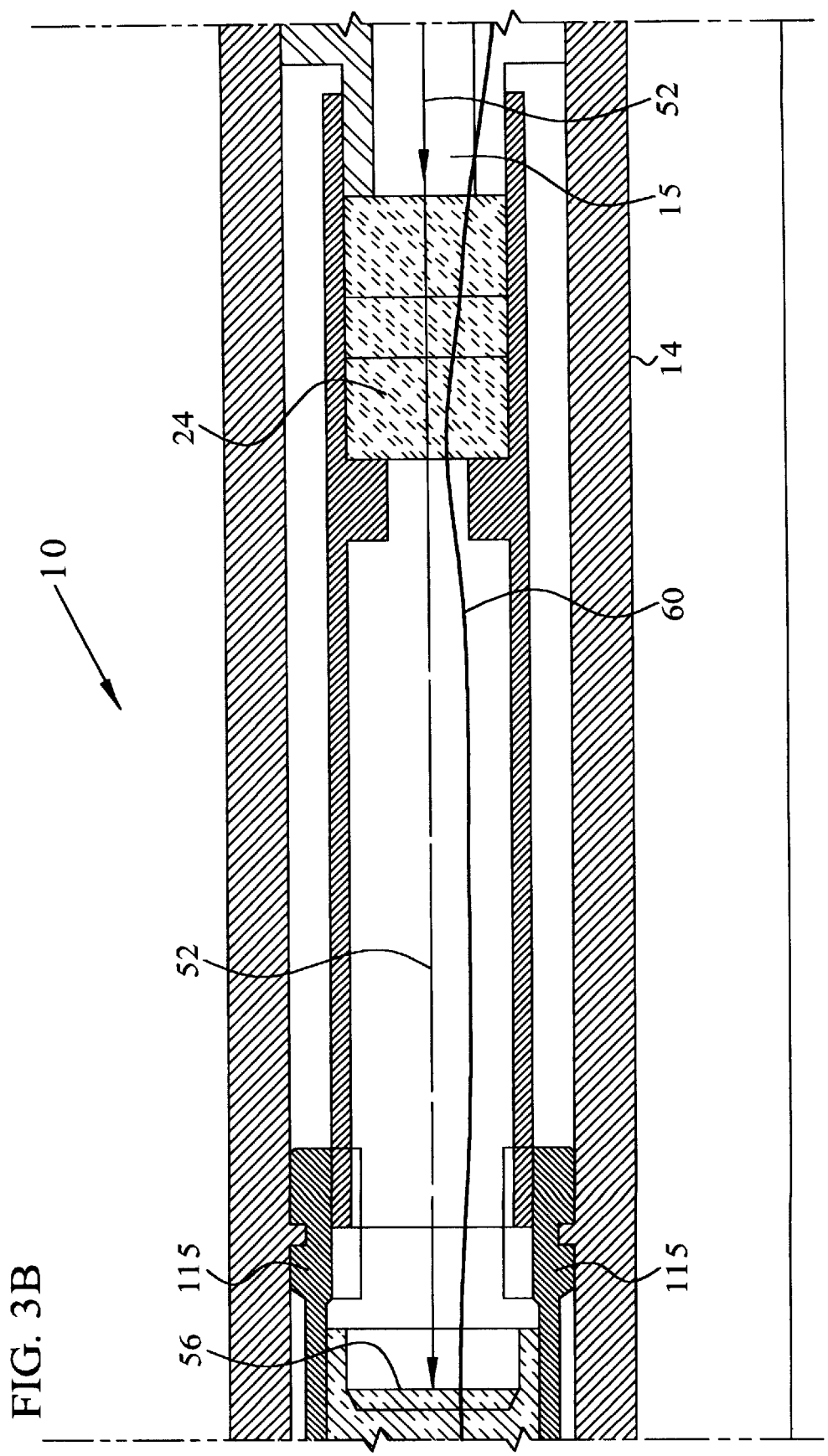
Figure 3C:
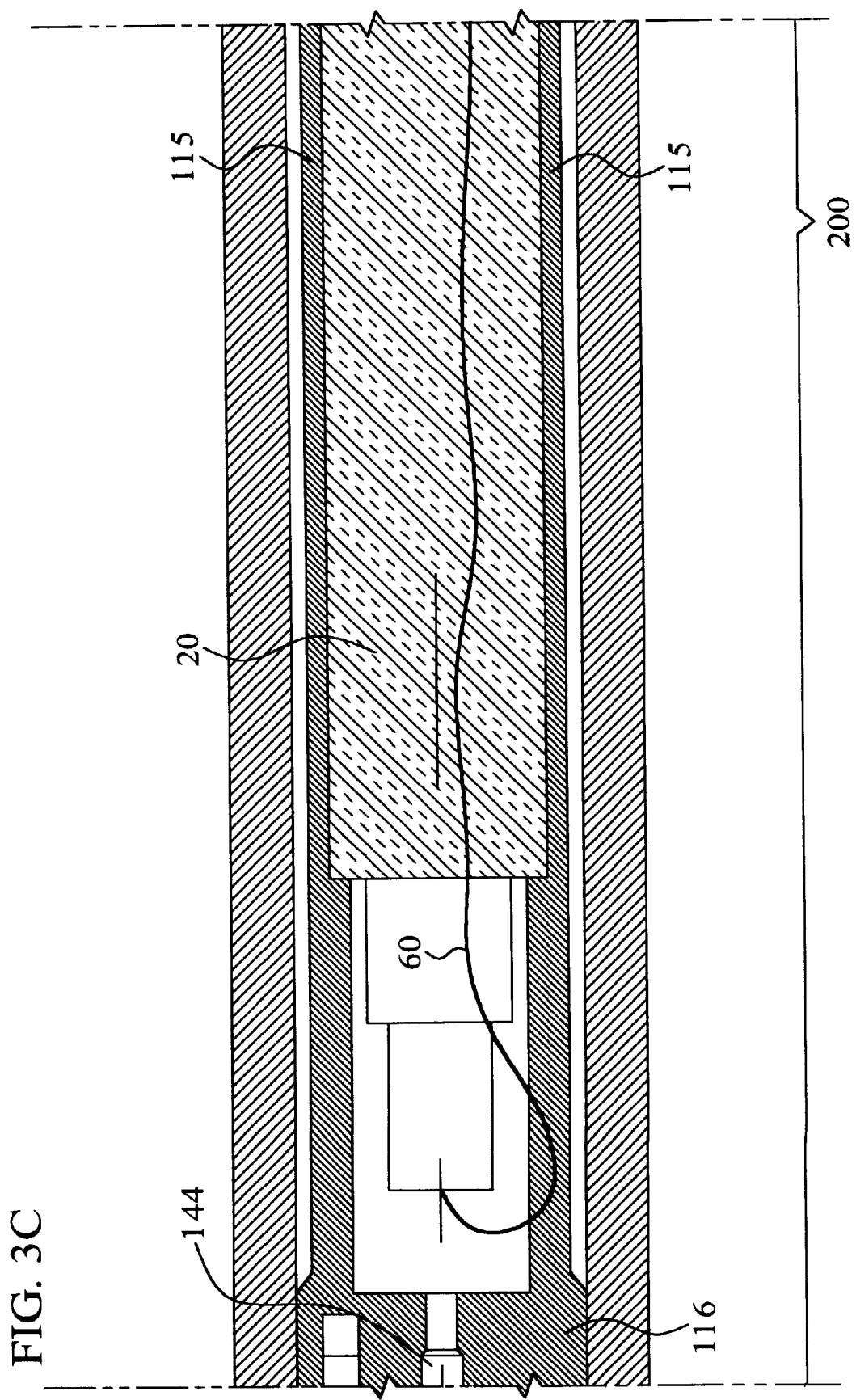
Figure 3D:
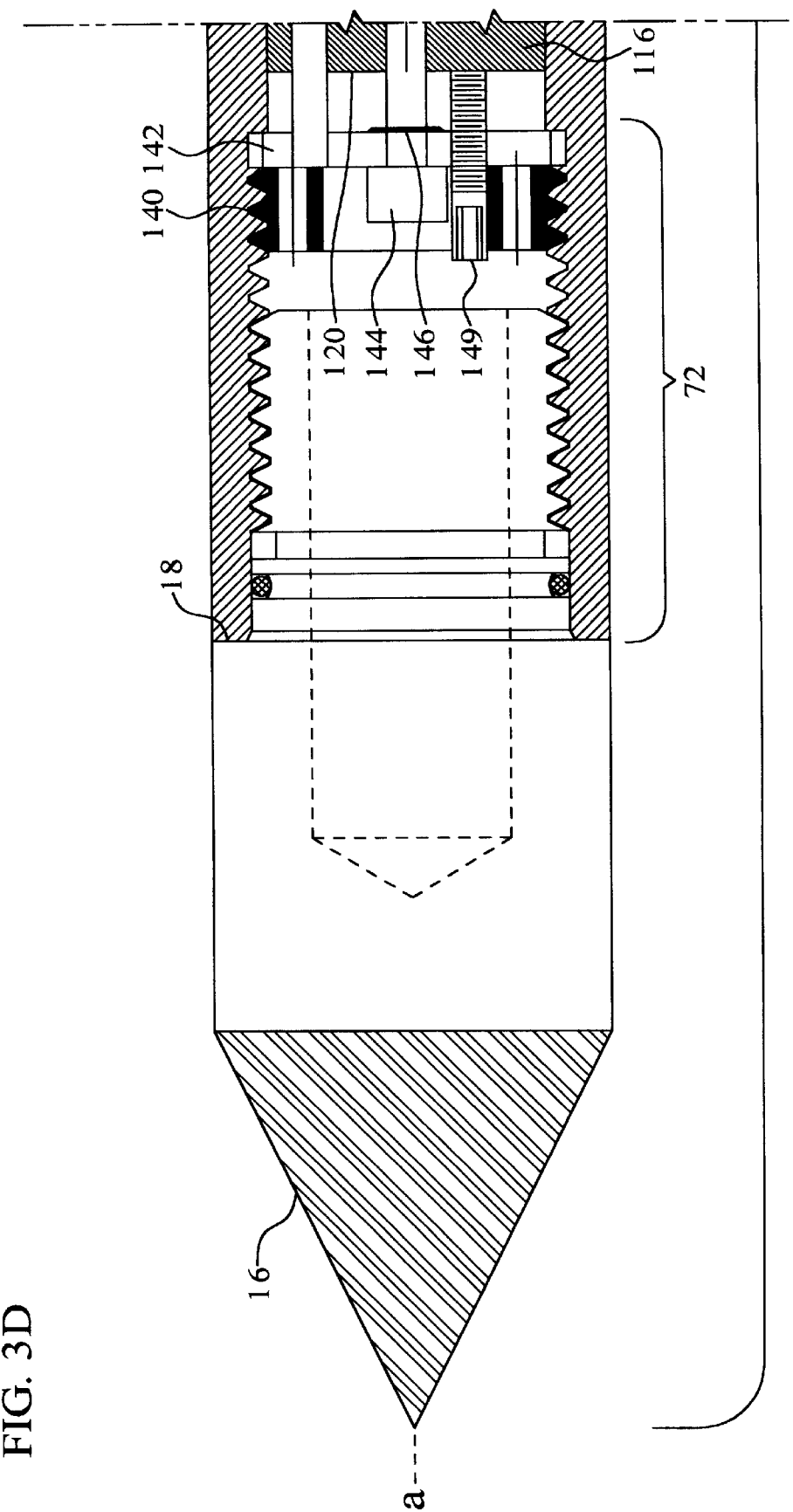
Figure 4:
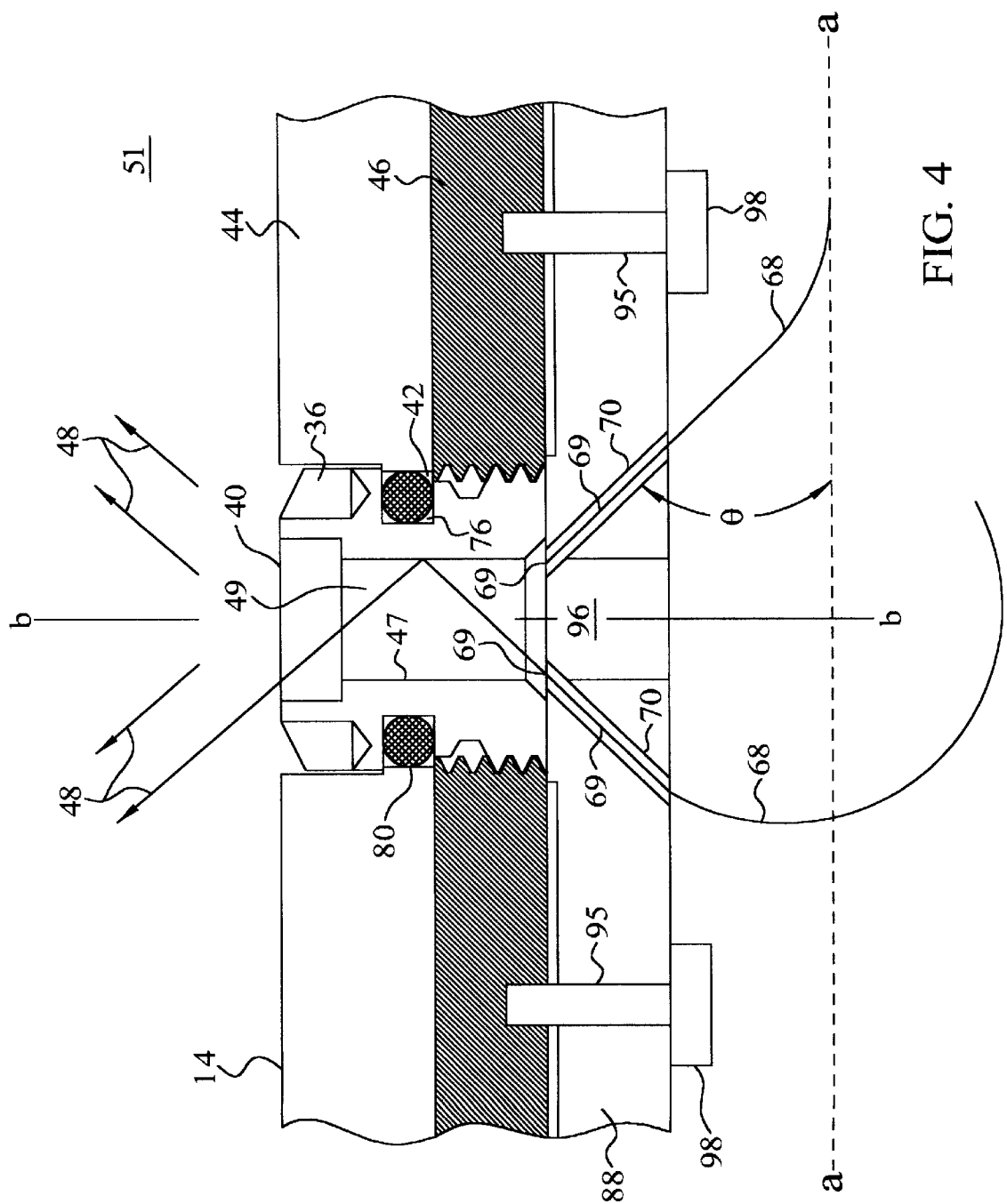
FIG. 4 is an enlarged view of the window housing illumination structure.

As shown in FIG. 3, the mirror 28 is mounted to mirror support 104 of the terminator insert 46 so that when terminator insert 46 is fitted in bore 15 of the tube 14: 1) the reflecting surface 108 of mirror 28 reflects light signals 52 through lens system 24 to the image gathering surface 56 of the camera 20; and 2) the window housing 36, attached to terminator insert 46, fits through aperture 42.

Figure 17:
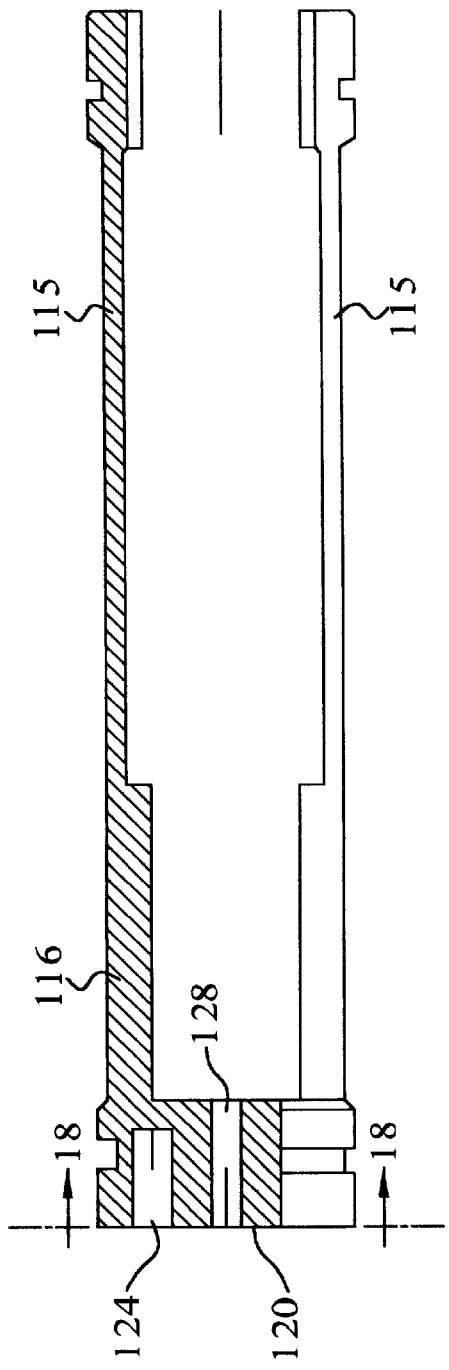
FIG. 17 shows the fork support.
Figure 18:
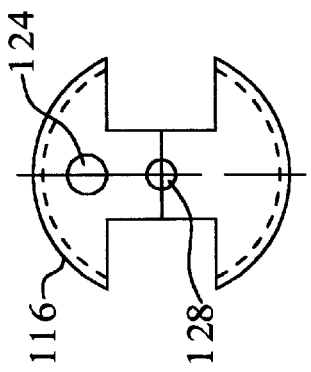
FIG. 18 is an end view of the fork support shown in FIG. 17.

By way of example, the camera 20 is fixedly mounted between two tines 115 of fork support 116, as shown in FIG. 3, preferably using an adhesive, not shown. The fork support 116 may be implemented as shown in FIGS. 17–18. Then the fork support 116 and camera 20 are slid inside bore 15 of tube 14 to precisely position the image gathering area 56 of camera 20 with respect to the lens system 24. The end 120 of fork support 116 includes a threaded aperture 128 and a bore 124.

Figure 19:
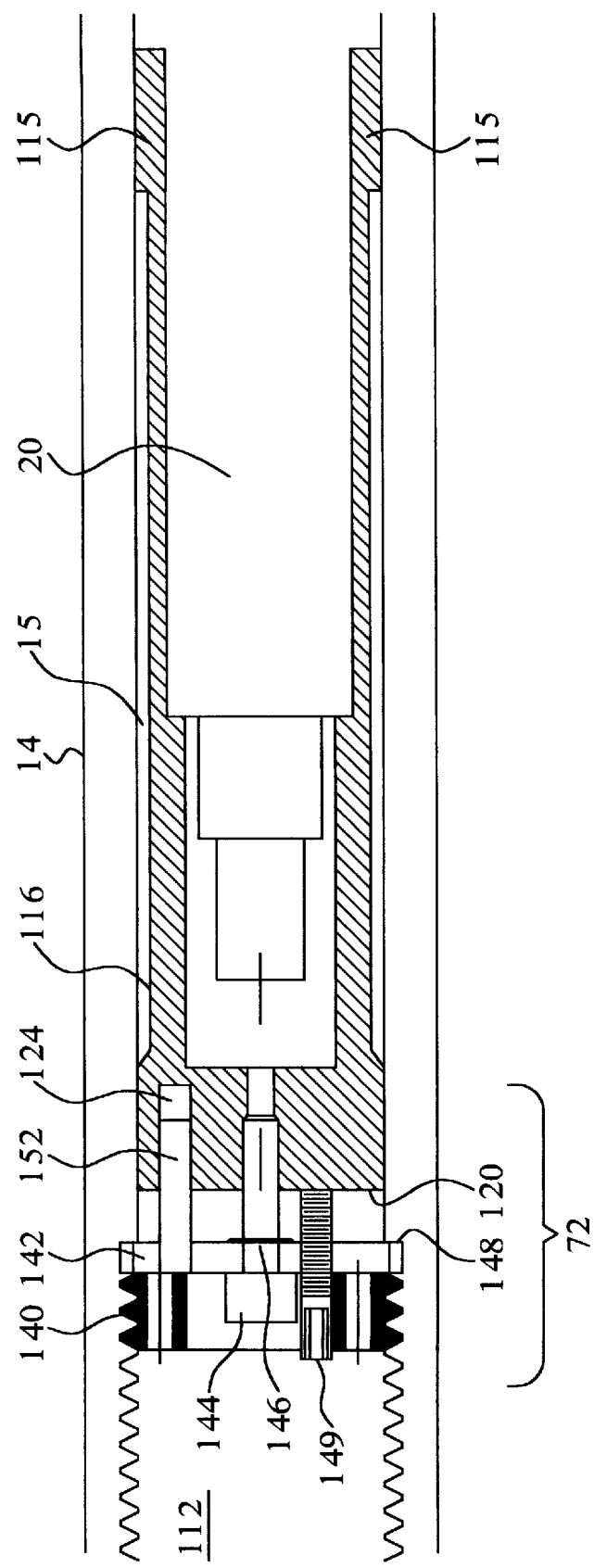
FIG. 19 is an enlarged view of the focusing system.
Figure 20:
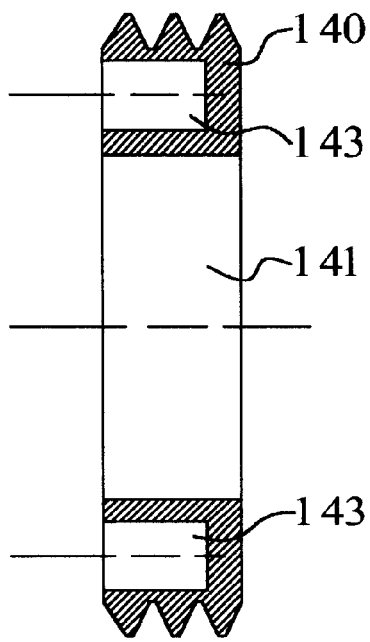
FIG. 20 is a side view of the jam nut.
Figure 21:
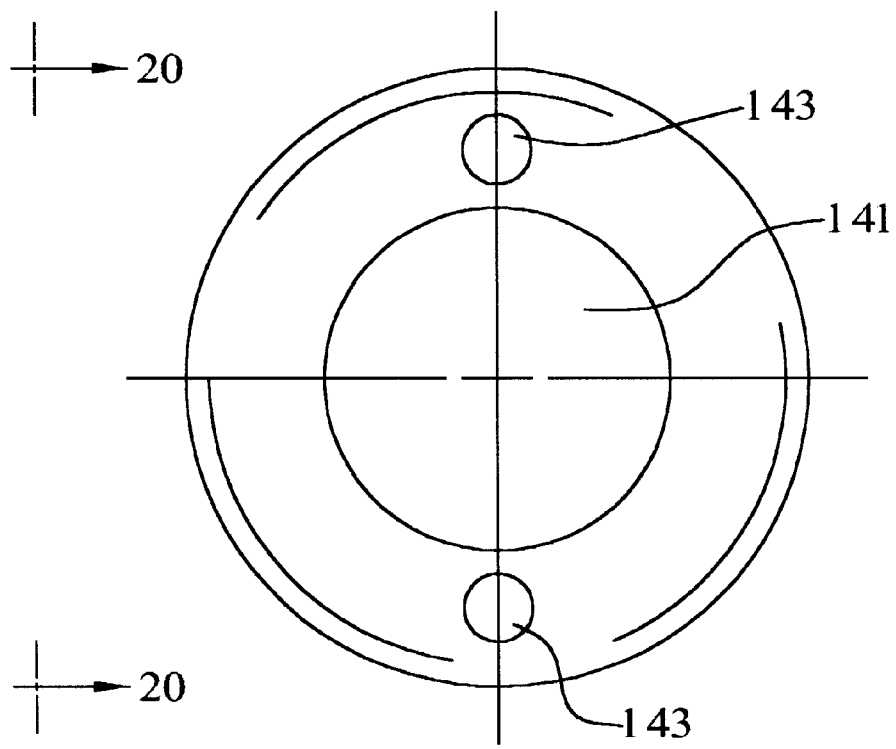
FIG. 21 is a front view of the jam nut of FIG. 20.
Figure 22:
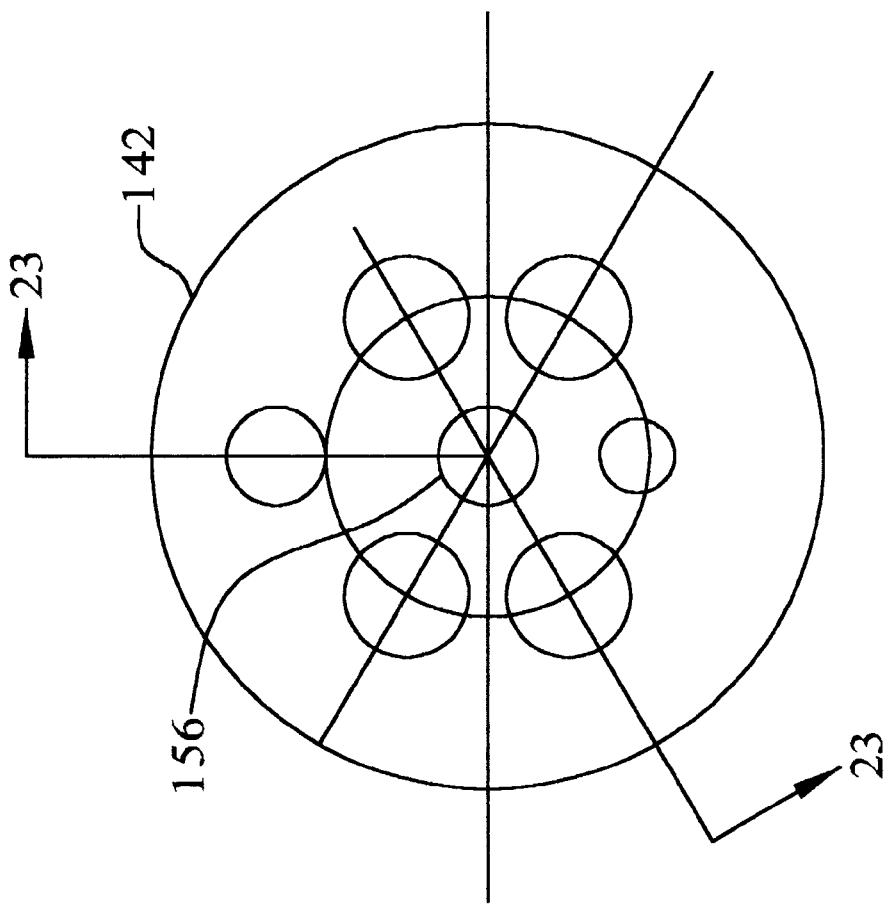
FIG. 22 shows the anchor plate.
Figure 23:
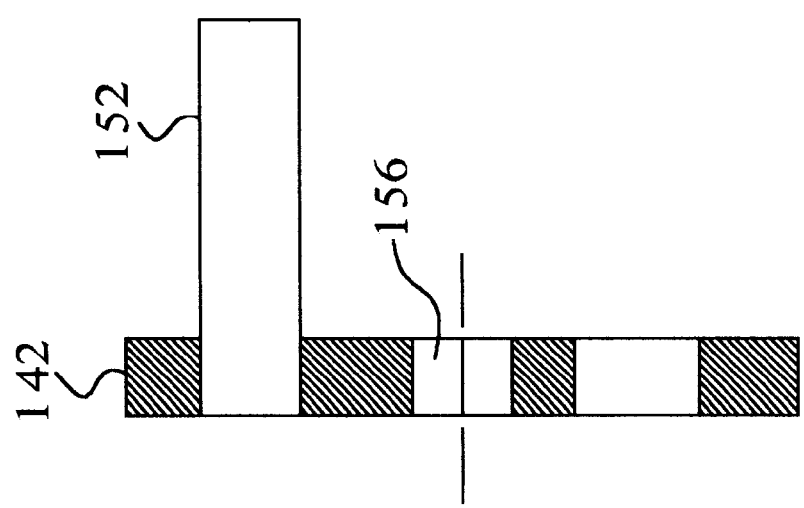
FIG. 23 is a side view of the anchor plate of FIG. 22.
Figure 24:
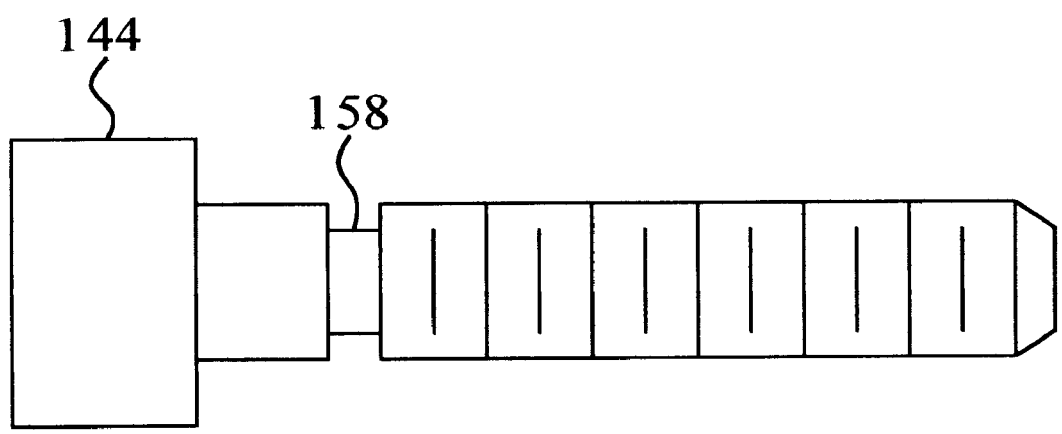
FIG. 24 shows the adjusting screw.

As shown in FIG. 3, light signals 52 are focused onto the image-gathering surface 56 of camera 20 by adjusting the distance between the image-gathering area 56 and the lens system 24 using focus system 72. Focus system 72, shown in FIG. 19, includes a jam nut 140 [FIGS. 20–21], anchor plate 142 [FIGS. 22–23], adjusting screw 144 [FIG. 24], retaining ring 146, and set screw 149. Adjustment of the position of camera 20 is accomplished by placing anchor plate 142 against land 148 of bore 112 in tube 14 so that pin 152, which is staked to anchor plate 142, extends into bore 124 of fork support 116. Pin 152 prevents fork support 116 from rotating in bore 15 of tube 14. Adjusting screw 144 is inserted through aperture 156 of anchor plate 142 and then retaining ring 146 is fitted in slot 158 of adjusting screw 144 so that the adjusting screw cannot slip out of aperture 156 of anchor plate 142. Then jam nut 140 is threaded into bore 112 of tube 14 using a spanner wrench (not shown) fitted into bores 143 so that the jam nut tightly seats against anchor plate 142 thereby fixing the anchor plate 142 relative to tube 14. Adjusting screw 144 may then be turned to vary the distance between video camera 20 and lens system 24 until light signals 52 are sharply focused onto image-gathering area 56 of video camera 20. The set screw 149 is then advanced against surface 120 of fork support 116 to fix the distance between the image gathering area 56 of camera 20 with respect to the lens system 24.

Figure 25B:
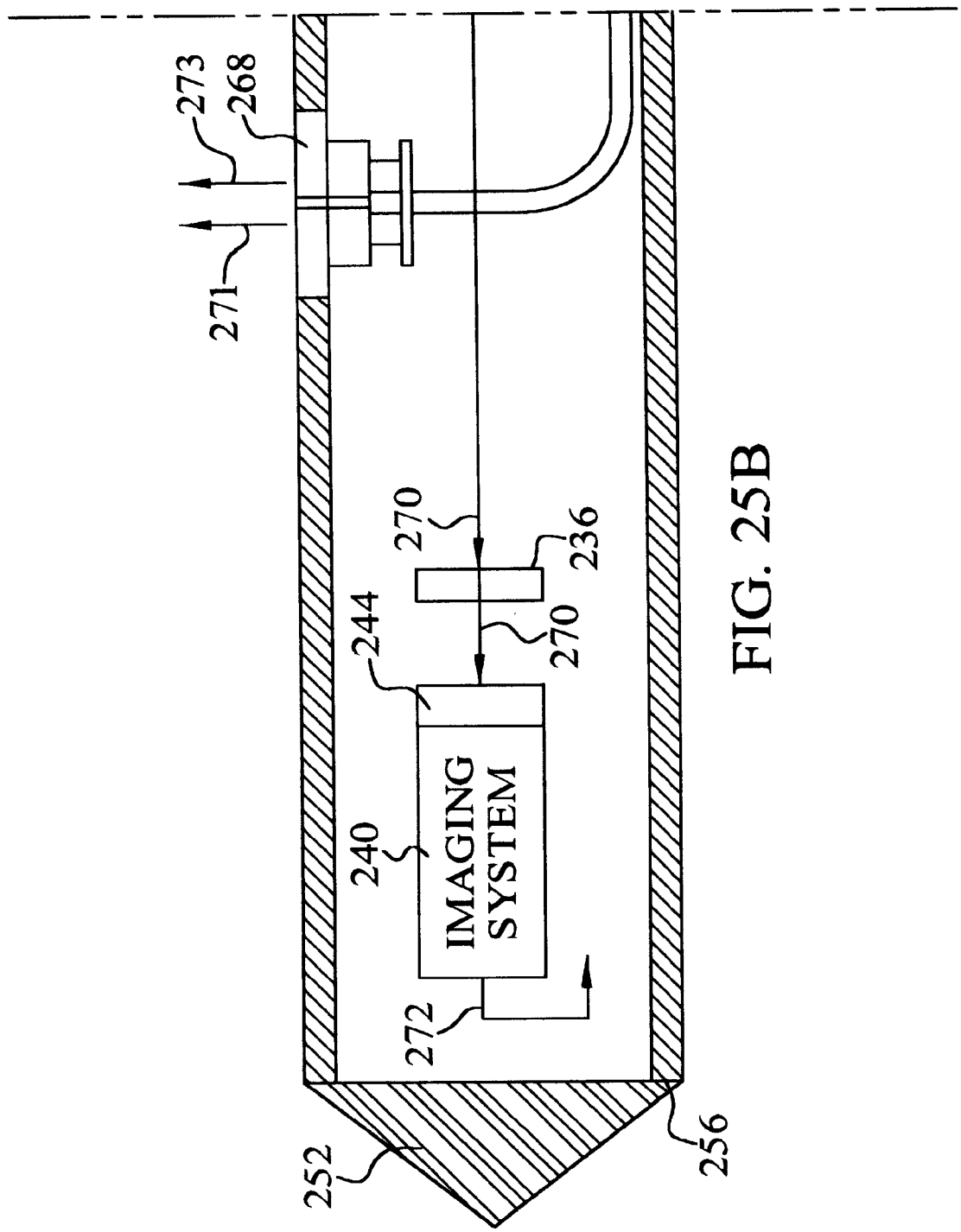
Figure 26:
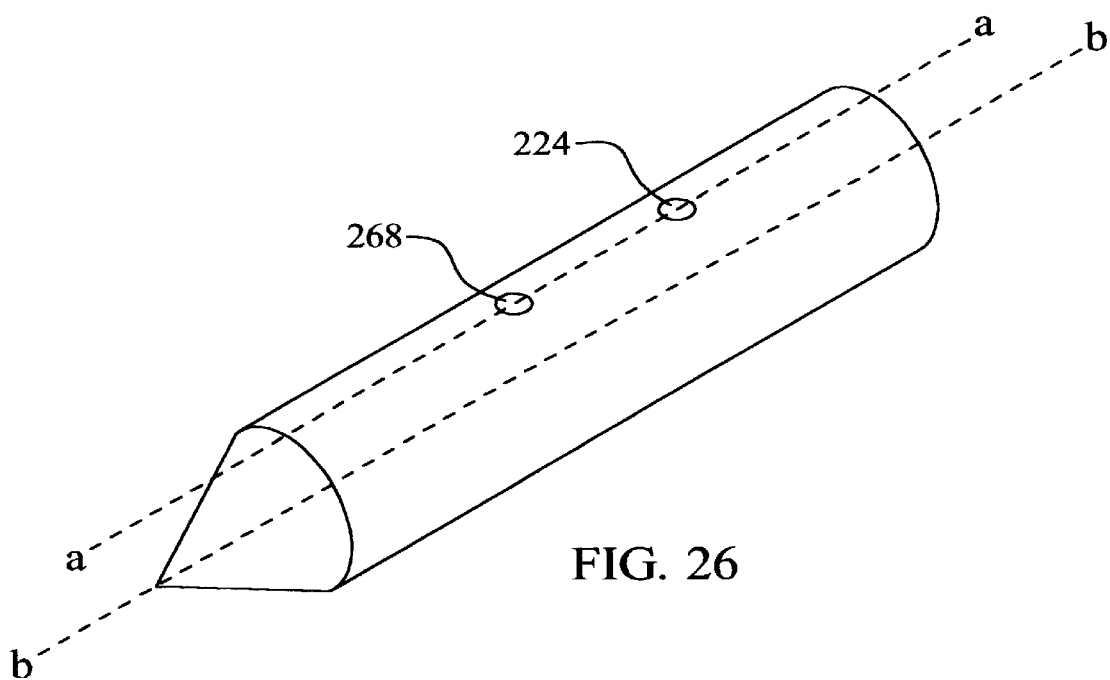
FIG. 26 is a three-quarter exterior view of the system shown in FIG. 25.

In FIG. 25 there is shown microscope imaging system 200 further including an indicator reagent delivery system comprising a pump system 264 which pumps a reactive fluid 271 through a preferably flexible tube 266 connected through the end 267 of the tube 248 to a nozzle 268. The tube 268 preferably may be implemented as ⅛ inch diameter polypropylene tubing and have an inside cross-sectional area of about 0.005 in$^2$. Such tubing has a working pressure of 350 psig and a burst pressure of 1400 psig. The nozzle 268 is mounted through the sidewall 258 of tube 248 so that the indicator reagent 271 may be dispensed or pumped from the nozzle 268 into the surrounding soil strata. The indicator reagent 271 is selected to chemically react with certain types of chemicals or micro-biological organisms of interest that may be present in the soil so that they may more easily be detected when illuminated due to a fluorescence or colorometric response of the complex. The nozzle 268 is preferably mounted through the sidewall 258 of tube 248 between the conically shaped tip 252 and window 224 so that, as shown in FIG. 26, the window 224 and nozzle 268 are generally located on a line a—a located on the surface of the tube 248 which is parallel to the longitudinal axis b—b of the tube 248. Therefore, indicator reagent is present in the soil by the time the reagent impregnated soil is viewed through the window 224 as the tube 248 is driven through the soil.

Figure 27:
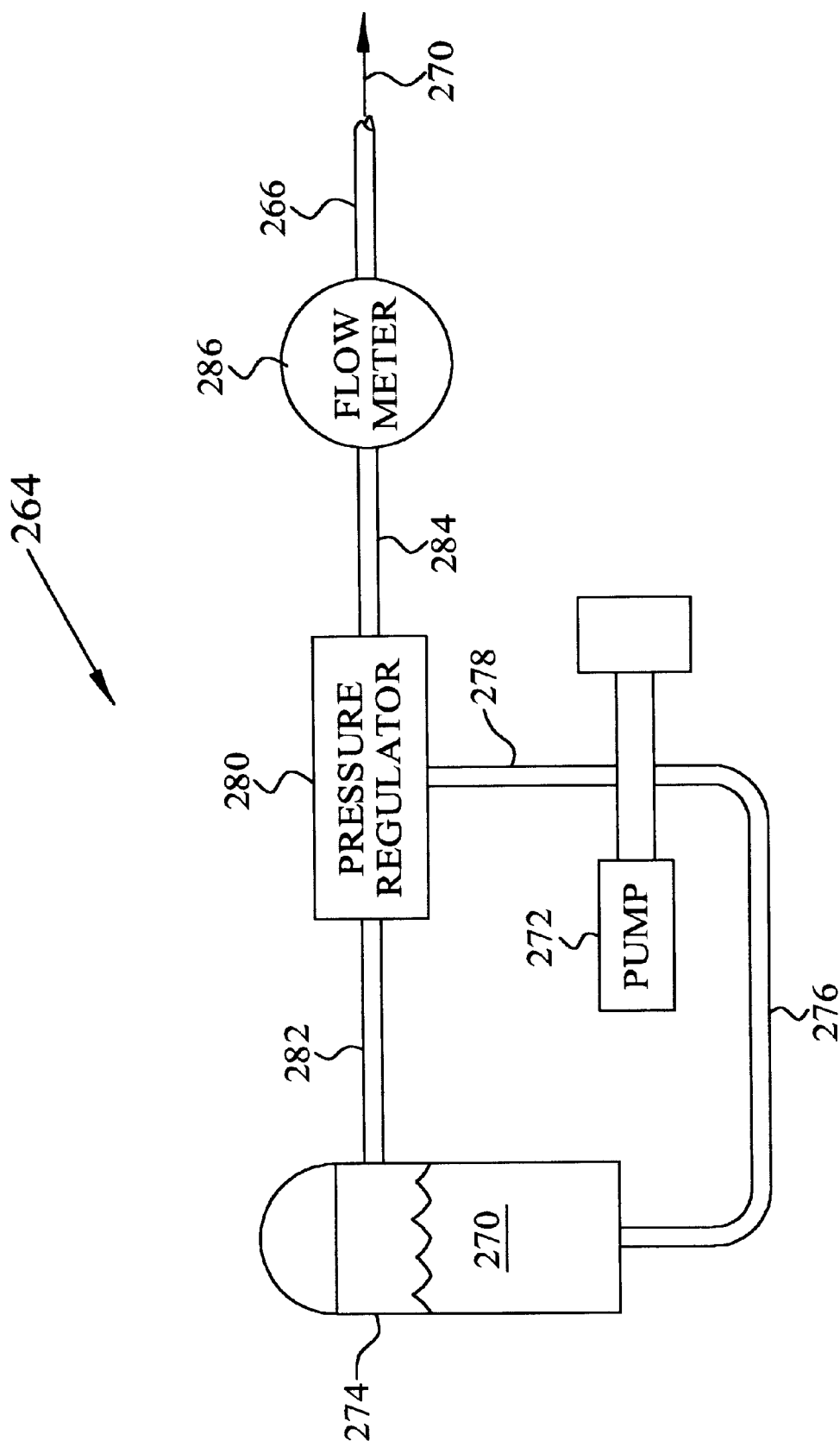
FIG. 27 is a schematic diagram of the indicator reagent delivery system of FIG. 25.

Pump circuit 264, shown in FIG. 27, includes a pump 272 which draws indicator reagent 271 from reservoir 274 through supply line 276 and outputs pressurized indicator reagent 271 through pump output line 278 to pressure regulator 280. The pressure regulator 280 regulates the pressure of indicator reagent agent 271 by, inter alia, returning some indicator reagent 271 back to reservoir 274 through bypass flow return line 282. The pressure regulator outputs indicator reagent 271 having a predetermined pressure, via line 284, to flow meter 286 which controls the volume flow of the pressurized indicator reagent 271. The flow regulated output of indicator reagent 271 is delivered to nozzle 228 via conduit 266. The pump may be a Neptune Model 535-S-N3 positive displacement piston/diaphragm pump having stainless steel internal elements, a Teflon™ diaphragm, and inert Viton™ seals so that the pump is chemically resistant to the indicator reagent 271. Like the pump 272, the pressure regulator 280 and flow meter 286 should be corrosion and chemically resistant to the indicator reagent 271. An example of a flow meter suitable for many applications of the invention is a polypropylene bellows type flow meter of the type manufactured by Gorman-Rupp which can accurately regulate the flow of indicator reagent 271 through nozzle 268 from 1.9 ml/min to 5200 ml/min.

Figure 29:
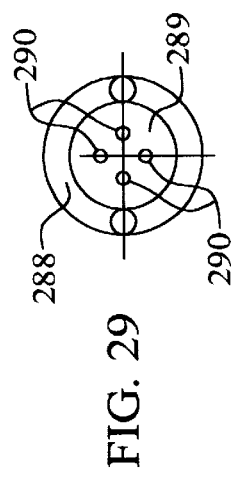
FIG. 29 is a plan view of the nozzle depicted in FIG. 28.
Figure 28:
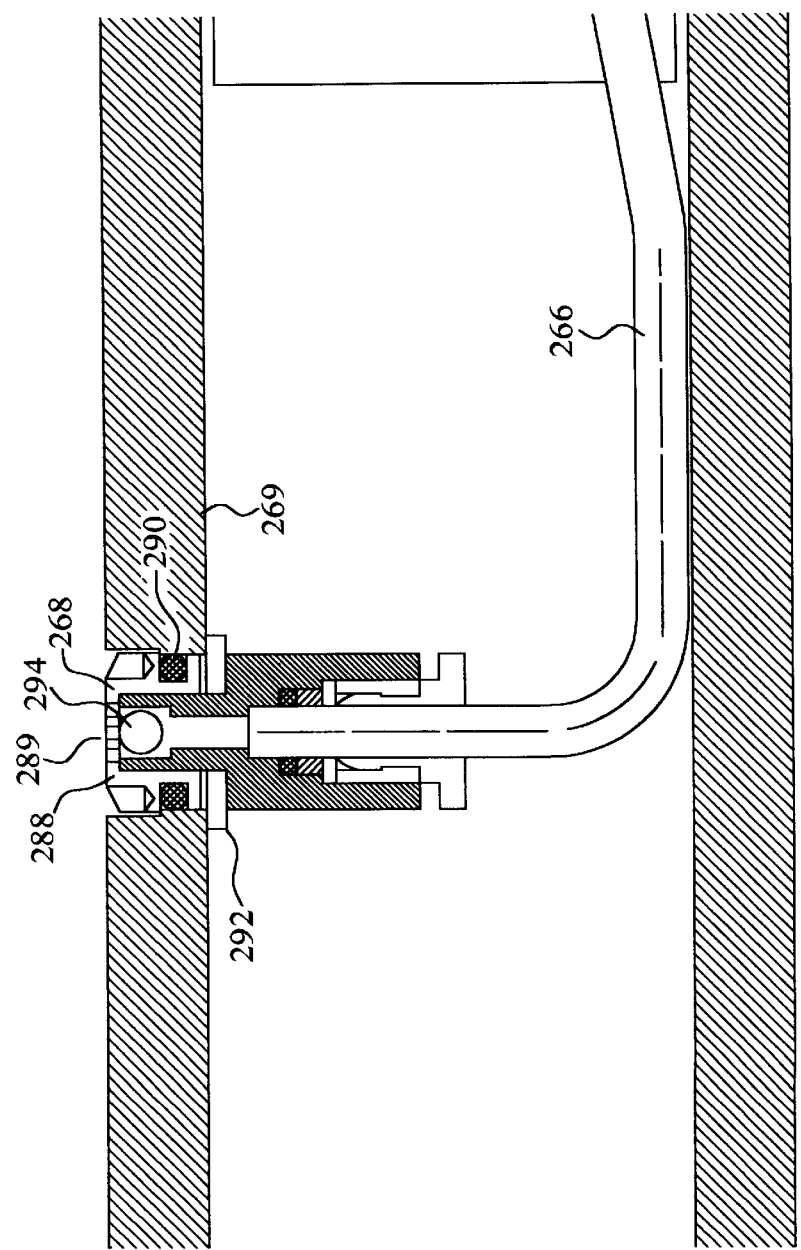
FIG. 28 shows the nozzle assembly of the fluid delivery system used in conjunction with the system shown in FIG. 25.

By way of example, as shown in FIG. 28, the nozzle 268 may be implemented as a Prestolok Fitting No. 68PL-2-1-X32 which is positioned through the tube wall 258 using a threaded check housing 288 which includes an O-ring seal 290 that prevents leakage into the tube 248. A contoured washer 292 is positioned between the nozzle 268 and the interior surface 269 of the tube 248 to maintain a tight surface interface between the interior surface 269 and nozzle 268. The nozzle is partially bored out to receive a stainless steel check-ball 294 between the nozzle and the check housing 288. The check-ball 294 prevents external hydrodynamic pressure from forcing fluids from the soil from entering the tube 248. However, the check-ball 294 allows indicator reagent 271 to be pumped out of the nozzle 268. The face 289 of the check housing may include one or more bores 290 through which agent 271 may be pumped. As shown in FIG. 29 by way of example, the check housing may include four bore 290 each having a diameter of about 0.047 inches to provide a combined flow area of 0.007 in$^2$. The slightly larger cross-sectional area of the bores 290 compared to that of the tube 266 allows any excessive external ground water pressure to force the check ball 294 to seal off the nozzle 268 from ground water contamination. It is to be understood, however, that the number, pattern, and size of the bores 290 through the face 288 of the check housing 288 may be configured to assure adequate diffusion of the indicator reagent 271 into the surrounding soil at for example, a pressure which preferably is greater than about 100 psig.

The indicator reagents employed in conjunction with the present invention are compounds that form either colored or fluorescent complexes with the analyte (chemical or biological) to be analyzed. The indicator reagents chemically react (or in chemical terms "complex") the chemical species (e.g., a metal ion) or some compound contained in the biological material (e.g., the DNA) of interest to form a new species (e.g., the indicator reagent and metal ion, or indicator reagent and DNA) having an optical response different from that of the uncomplexed analyte or indicator reagent by itself. An example of a common indicator reagent is the pH indicator "phenolphthalein." When a drop of phenolphthalein (which is clear in color) is added to water, the phenolphthalein molecule forms a red colored complex with the hydrogen ions in the water. Since the hydrogen ion concentration in water determines the pH, the intensity of color generated from the complex formed by the phenolphthalein and hydrogen is a direct indicator of the pH of the water.

A suitable class of indicator reagents 271 are fluorescent indicator reagents that form fluorescent complexes with analytes such as heavy metals and cations such as Na+, K+ and Ca++. Examples of other fluorescent indicator reagents 271 are specific for the nucleic acids contained in microbiological organisms. Common examples of fluorescent indicator reagents may based on the quinolines such as hydroxyquinoline-5-sulfonic acid, 8-hydroxyquinoline, 2-methyl-8-hydroxyquinoline, N-(6-methoxy-8-quinoyl)-para-toluene sulfonamide and p-tosyl-8-amino quinoline. Molecules of these examples form fluorescent complexes with metals such as zinc, cadmium, magnesium, etc. Also, there are a wide range of fluorescent nucleic acid stains that form fluorescent complexes with the nucleic acids contained in the cells of the microbiological organisms. Specific examples of such fluorescent indicators, or nucleic acid stains, include the cell-permeant SYTO® indicator reagents for labeling DNA and RNA in living cells including mammalian cells, fungi and bacteria. Other examples of florescent indicator reagents include cell-impermeant SYTOX® Green nucleic acid stains that penetrate cells with compromised plasma membranes. SYTO® indicator reagents and SYTOX® Green nucleic acid stains are available from Molecular Probes, Inc. of Eugene, Oreg. Fluorescent indicators that may be used to detect the presence of nucleic acids include, by way of example, hexidium iodide (a lipophilic phenthridiium dye) and hydroxystilbamidine.

In addition to fluorescent indicator reagents, there is also a family of "indicator reagents" based on the formation of colored coordination compounds. These compounds form "colored" rather than fluorescent complexes with a suitable analyte of interest. Ethylenediaminetetraacetic acid (EDTA) is an example of an indicator reagent that forms colored complexes with metals such as copper. Nitrilotriacetic acid (NTA) is an example of an indicator reagent that forms colored complexes with metals such as nickel and copper.

In order to account for the possible variations in the amount of indicator reagent which may be dispensed into the surrounding soil structure, a chemical tracer 273 which is non-reactive with the analyte can be added to the indicator reagent. Thus, both an indicator reagent 271 and chemical tracer 273 may be dispensed from pump system 264 of FIG. 25 and pump 272 of FIG. 30. The non-reactive (chemical tracer is spectroscopically distinguishable from the indicator reagent and analyte (species of interest) and is used to normalize the optical response due to differences in the concentration of indicator reagent present in the soil. Such normalization may be determined from the ratio of the intensities of the spectral responses of the complex (the chemical product of the analyte and indicator reagent) and the chemical tracer 273. Examples of tracer chemicals are rhodamine 6G and quinine sulfate.

Figure 30:
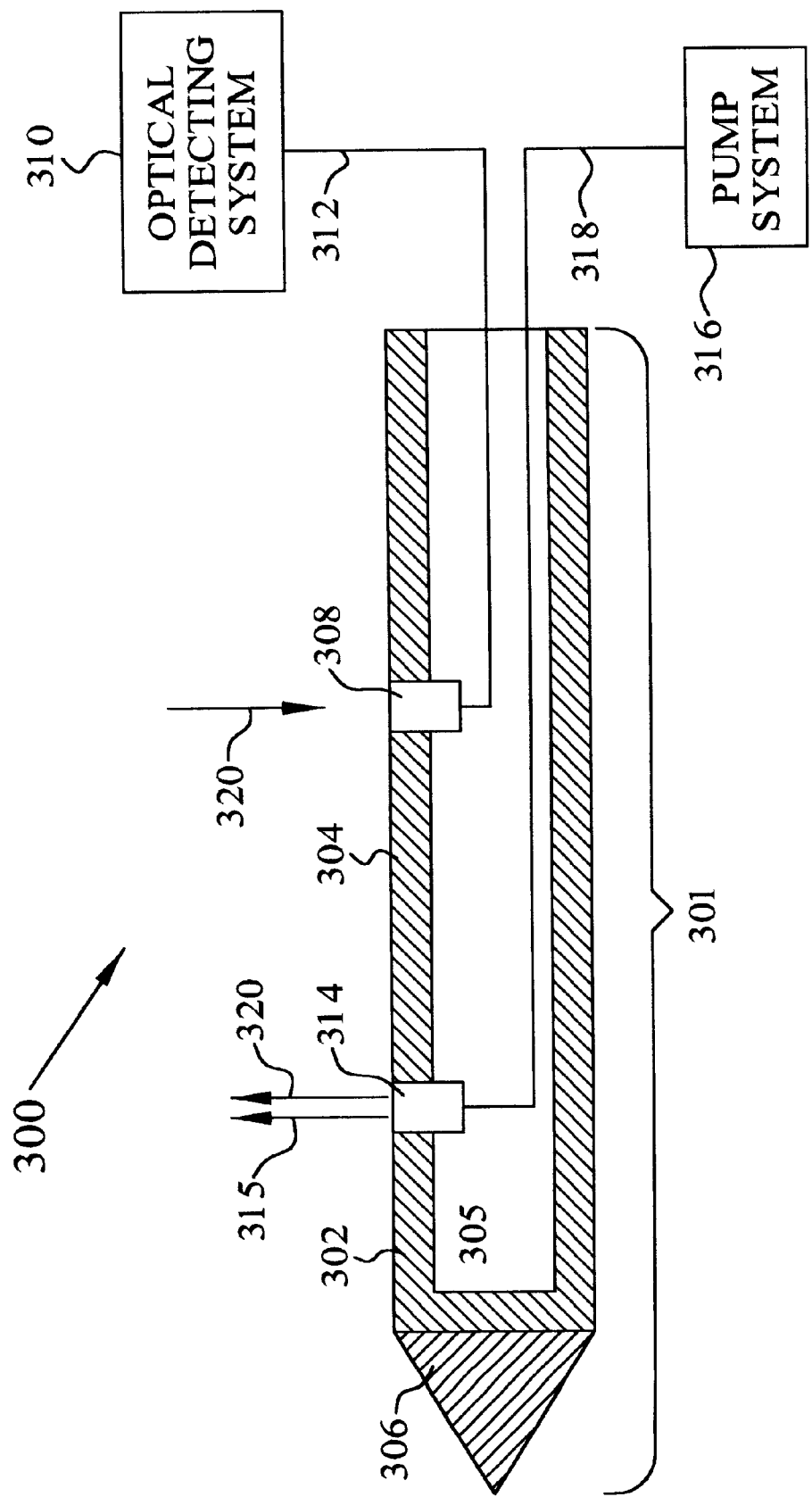
FIG. 30 is a cross-sectional/block diagram of another embodiment of an optical detecting system which includes an indicator reagent agent delivery system.

Another embodiment of an optical detecting system 300 which includes a reactive agent delivery system is described with reference to FIG. 30. The system includes a cone penetrometer 301 comprising a generally cylindrical body 302, preferably made of a hardened steel, to which is mounted a conically shaped hardened tip 306. The cylindrical body 302 has a tube wall 304 and a bore 305. An optical window 308 and fluid nozzle 314 are mounted through the tube wall 302 such that the nozzle 314 is positioned between the conical tip 306 and the window 308. By way of example, the window 308 may be made of sapphire, a relatively hard material, so that abrasion damage to the window 308 is minimized as the penetrometer is driven into the surrounding subsoil environment, not shown. An optical fiber 312 optically interconnects the window 308 and an optical detecting system 310. Pump system 316 pumps indicator reagent 315 through tube 318 and out of nozzle 302 into the surrounding soil structure. In some application, it may be desirable for pump system 316 to further dispense a chemical tracer 320 along with the indicator reagent for the reasons described above with reference to chemical tracer 273. Any light signals 320 which pass through window 308 propagate via optical fiber 312 to optical detecting system 310 which may include, for example, a CCD camera, a photo detector such as a photo diode array, or a photo multiplier tube.

Although the invention has been described with reference to specific embodiments, numerous variations and modifications of the invention may become readily apparent to those skilled in the art in light of the above teachings. For example, the light source 64 shown in FIG. 3 may be mounted within tube 14 or may be located remotely from the tube. Moreover, the invention may employ chemical indicator reagents that produce either a decrease or increase in an optical signal for an analyte of interest. Examples of alternative indicators include: (1) reagents that produce chemiluminescent signals without external optical stimulation; and (2) reagents that quench the specific fluorescence of the analyte of interest. Furthermore, the light source and/or pump system, including the reservoir may be mounted within the probe, or externally with respect to the probe. Further, the reagent could be pumped from the surface to outlet ports on the probe, or be contained in a reservoir mounted within the probe itself. Additonally, the pump system may be used to dispense one or more indicator reagents in combination or serially, as well as one or more tracer compounds. Therefore, it is to be understood that the invention may be practiced other than as specifically described.

We claim:

1. A microscope imaging system, comprising,
    a tube including a longitudinal bore and a sidewall having an aperture;
    a light source for generating first light signals;
    a window housing mounted to said tube and fitted through said aperture, said window housing having an optical transit bore with a light diffusing surface for reflecting and diffusing said first light signals, whereupon said first light signals are transformed into diffused light signals;
    an optical fiber for directing said first light signals to diffusely reflect off said light diffusing surface;
    an optically transparent window mounted to said window housing within said optical transit bore through which said diffused light signals propagate; and
    an optical detector for detecting second light signals which enter said longitudinal bore through said window.

2. The microscope imaging system of claim 1 further including a conically shaped tip mounted to a first end of said tube.

3. The microscope imaging system of claim 1 wherein said optical detector is an optical imaging system positioned in said bore.

4. The microscope imaging system of claim 3 further including a first lens system for focusing said second light signals onto said imaging system.

5. The microscope imaging system of claim 4 further including an optically reflective element for directing said second light signals from said window to said first lens system.

6. The microscope imaging system of claim 4 wherein said first lens system has a variable focal length.

7. The microscope imaging system of claim 3 further including an optical filter between said imaging system and said first lens system for selecting spectral components of said second signals.

8. The microscope imaging system of claim 1 further including a second lens system for directing said first light signals into said optical fiber.

9. The microscope imaging system of claim 8 further including an optical filter between said second lens system and said light source for selecting spectral components of said first light signals.

10. The microscope imaging system of claim 1 wherein said light source includes a laser.

11. The microscope imaging system of claim 1 wherein said light source includes a flash lamp.

12. The microscope imaging system of claim 3 wherein said imaging system includes a camera.

13. The microscope of claim 3 wherein said imaging system includes a video camera.

14. The microscope imaging system of claim 1 further including a fluid delivery system for dispensing an indicator reagent from said tube for reacting with an analyte having first optical response characteristics to form a complex having second optical response characteristics different from said first optical response characteristics.

15. The microscope imaging system of claim 14 wherein said fluid delivery system dispenses a tracer chemical with said indicator reagent, whereby said tracer chemical is spectroscopically distinguishable from said complex.

16. The microscope imaging system of claim 14 wherein said fluid delivery system includes:
   a reservoir for storing said indicator reagent; and
   a pump for pumping said indicator reagent.

17. The microscope imaging system of claim 16 further including a pressure regulator for regulating the pressure of said indicator reagent output by said pump.

18. The microscope imaging system of claim 16 further including a flow meter for controlling the flow of said indicator reagent.

19. The microscope imaging system of claim 14 wherein said fluid delivery system includes a nozzle mounted through said sidewall of said tube through which said indicator reagent is dispensed.

20. An optical detection system, comprising,
   a tube including a longitudinal bore and a sidewall having an aperture;
   a light source for generating first light signals;
   a window housing mounted to said tube and fitted through said aperture, said window housing having an optical transit bore with a light diffusing surface for reflecting and diffusing said first light signals, whereupon said first light signals are transformed into diffused light signals;
   an optical fiber for directing said first light signals to diffusely reflect off said light diffusing surface;
   an optically transparent window mounted to said window housing within said optical transit bore through which said diffused light signals propagate;
   an optical detector for detecting second light signals which enter said longitudinal bore through said window; and
   a fluid delivery system for dispensing an indicator reagent from said tube.

21. The optical detection system of claim 20 wherein said indicator reagent reacts with an analyte having optical response characteristics to form a complex having optical response characteristics different from said optical response characteristics of said analyte.

22. The optical detection system of claim 20 wherein:
   said fluid delivery system includes a reservoir for storing said indicator reagent; and
   a pump for pumping said indicator reagent.

23. The optical detection system of claim 20 further including a pressure regulator for regulating the pressure of said indicator reagent that is output by said pump.

24. The optical detection system of claim 20 further including a flow meter for controlling the flow of said indicator reagent.

25. The optical detection system of claim 20 wherein said fluid delivery system includes a nozzle mounted through said sidewall of said tube through which said indicator reagent is dispensed.

26. The optical detection system of claim 20 further including a conically shaped tip mounted to a first end of said tube.

27. The optical detection system of claim 20 further wherein said optical detector is an optical imaging system.

28. The optical detection system of claim 20 further including a first lens system for focusing said second light signals onto said imaging system.

29. The optical detection system of claim 28 further including an optically reflective element for directing said second light signals from said window to said first lens system.

30. The optical detection system of claim 28 further including an optical filter interposed between said imaging system and said first lens system for filtering spectral components of said second signals.

31. The optical detection system of claim 20 further including a second lens system for directing said first light signals into said optical fibers.

32. The optical detection system of claim 31 further including an optical filter between said second lens system and said light source for filtering spectral components of said first light signals.

33. The optical detection system of claim 20 wherein said light source includes a laser.

34. The optical detection system of claim 20 wherein said light source includes a flash lamp.

35. The optical detection system of claim 20 wherein said first lens system has a variable focal length.

36. The optical detection system of claim 20 wherein said imaging system includes a camera.

37. The optical detection system of claim 20 wherein said imaging system includes a video camera.

38. The microscope imaging system of claim 20 wherein said fluid delivery system dispenses a tracer chemical with said indicator reagent.

39. The microscope imaging system of claim 38 wherein said tracer chemical is spectroscopically distinguishable from the combination of said indicator reagent and an analyte.

* * * * *